(12) United States Patent
Loewenheim

(10) Patent No.: US 7,087,581 B1
(45) Date of Patent: Aug. 8, 2006

(54) METHOD FOR THE TREATMENT OF DISEASES OR DISORDERS OF THE INNER EAR

(75) Inventor: Hubert Loewenheim, Tuebingen (DE)

(73) Assignee: Sound Pharmaceuticals Incorporated, Seattle, WA (US)

( * ) Notice: Subject to any disclaimer, the term of this patent is extended or adjusted under 35 U.S.C. 154(b) by 0 days.

(21) Appl. No.: 09/622,719

(22) PCT Filed: Feb. 23, 1999

(86) PCT No.: PCT/EP99/01153

§ 371 (c)(1),
(2), (4) Date: Oct. 18, 2000

(87) PCT Pub. No.: WO99/42088

PCT Pub. Date: Aug. 26, 1999

(30) Foreign Application Priority Data

Feb. 23, 1998 (DE) ................... 198 07 426

(51) Int. Cl.
*A61K 31/70* (2006.01)
*C07H 21/04* (2006.01)

(52) U.S. Cl. ........................ 514/44; 536/24.5
(58) Field of Classification Search ............ 435/6; 514/44, 2; 536/24.5
See application file for complete search history.

(56) References Cited

U.S. PATENT DOCUMENTS 5,962,224 A 10/1999 Shin et al.
6,066,652 A 5/2000 Zenner et al.

FOREIGN PATENT DOCUMENTS

| WO | 97/04762 | 2/1997 |
|---|---|---|
| WO | WO 97/04762 A1 | 2/1997 |
| WO | 97/17983 | 5/1997 |
| WO | 98/00014 | 1/1998 |
| WO | 98/13048 | 4/1998 |
| WO | 99/06064 | 2/1999 |

OTHER PUBLICATIONS

Ping Chen et al., DEVELOPMENT 126, pp. 1581-1590.*
Andrea D. Branch, TIBS 23 —Feb. 1998 pp. 45-50.*
Hubert Lowenhem et al., Proc. Natl. Acad. Sci. USA, vol. 96, pp. 4084-4088.*
Paul J. Hauser et al., Cell Growth & Differentiation, vol. 8, pp. 203-211.*
Sudhir Agrawal et al., Molecular Medicine Today, Feb. 2000, vol. 6, pp. 72-81.*
Douglas W. Green et al., J. Am. Coll. Surg. pp. 93-105.*
Kuang-Yu Jen et al., Stem Cells, 2000; 18: pp. 307-319.*
Markus Pfister et al., Gentherapeutische Aspekte am Innenohr, pp. 50-57.*
Chen, P. et al., "p27/Kipl, a Cyclin-dependent Kinase Inhibitor is Required for the Normal Development of the Mouse Auditory Sense Organ," *Society for Neuroscience Abstracts*, (1998) XP002123936 abstract.
Schweitzer V.G., "Cisplatin-Induced Ototoxicity: the Effect of Pigmentation and Inhibitory Agents" *Laryngoscope*, 103, pp. 1-52, (Apr. 1993), XP-002123937 abstract.
Umemoto M. et al., "Hair cell regeneration in the chick inner ear following acoustic trauma: ultrastructural and immunohistochemical studies," *Cell & Tissue Research*, vol. 3, pp. 435-443, (Spring 1995) XP-002060017 document.
Bujia, J. et al., "Immunohistochemical detection of proliferating cell nuclear antigen in middle ear cholesteatoma, " *Eur Arch Oto-Rhino-Laryngology*, 253: 21-24, (Spring, 1996) XP-002123938 abstract.
Yamuguchi, T. et al., "The Effect of Chalone on the Cell Cycle in the Epidermis During Wound Healing," *Exptl Cell Research*, 89: 247-254, (1974) XP-002123939 document.

(Continued)

*Primary Examiner*—Andrew Wang
*Assistant Examiner*—Tracy Vivlemore
(74) *Attorney, Agent, or Firm*—Christensen O'Connor Johnson Kindness PLLC

(57) ABSTRACT

In a process for the treatment of diseases or disorders of the inner ear linked with damage or destruction of sensory cells of the inner ear, for regenerating the sensory cells use is made of at least one active ingredient, which at least partly inhibits or eliminates the inhibiting action of at least one cell cycle inhibitor present in the inner ear. In this process the sensory cells of the inner ear are preferably regenerated by stimulating the proliferation of supporting cells. The sensory cells of the inner ear are so-called hair sensory cells. As cell cycle inhibitors use can be made of cyclin-dependent kinase inhibitors such as in particular the cyclin-dependent kinase inhibitor $p27^{Kip1}$.

3 Claims, 1 Drawing Sheet

OTHER PUBLICATIONS

Figure 1:
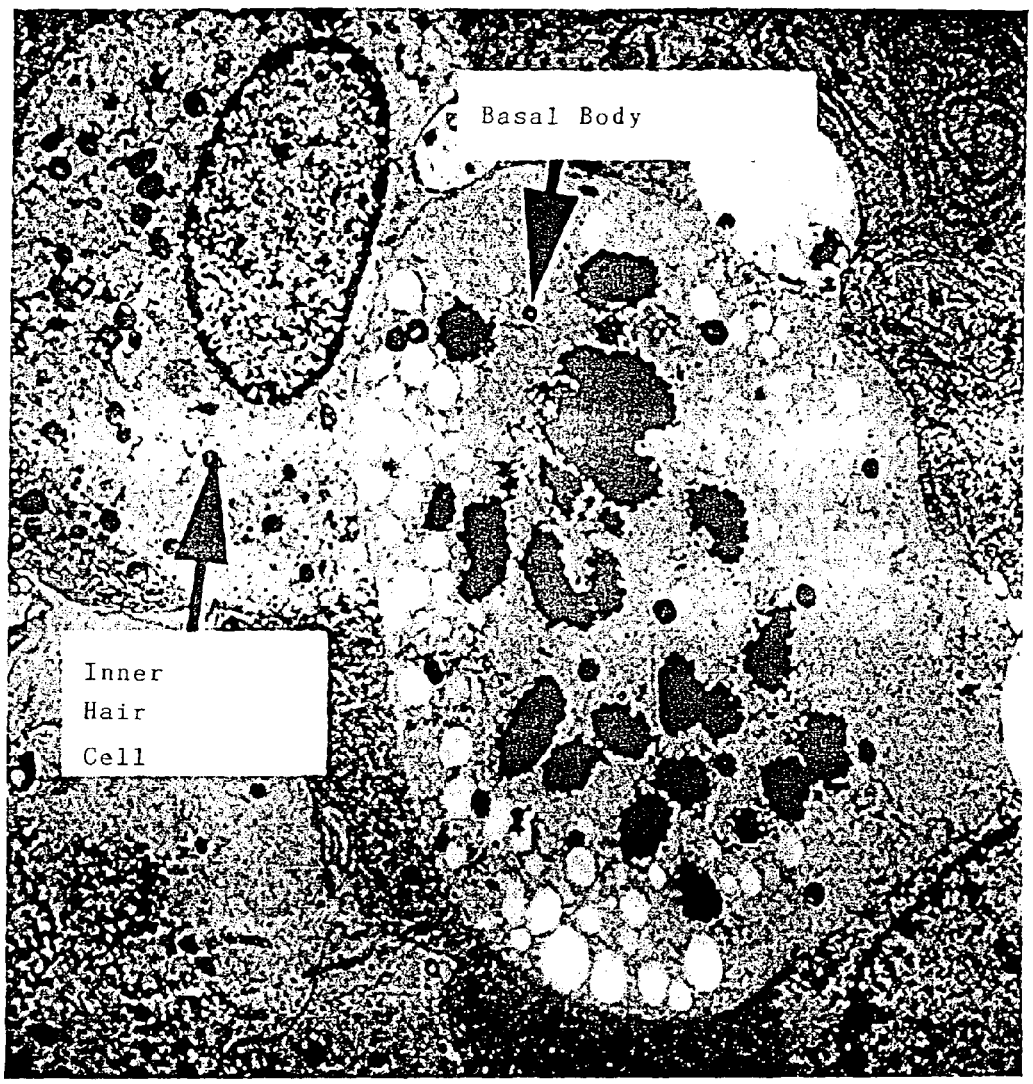

Spencer-Dene, B. et al., "Distribution of, and a putative role for, the cell-surface neutral metalloendopeptidases during mammalian craniofacial devlopment," *Development*, 120 (11) : 3213-26, (Nov. 1994).

Leon, Y. et al., "Developmental Regulation of Fos-Protein during Proliferative Growth of the Otic Vesicle and its Relation to Differentiation Induced by Retinoic Acid," *Developmental Biology*, 167: 75-86, (Jan. 1995).

Adler, H.J. et al., "New hair cells arise from supporting cell conversion in the acoustically damaged chick inner ear," *Neuroscience Letters*, 205: 17-20, (1996).

Birnbaum, J.E., et al., "Effects of Reserpine, Epidermal Growth Factor, and Cyclic Nucleotide Modulators on Epidermal Mitosis," *Journal of Investigative Dermatology* 66(05):313-318, 1976 (ACS Abstract No. 85:13565).

Dal Bo, A. and A. Pitotti, "The Effects of β-Lactoglobulin Genetic Variants A and B on the Funcitonal Properties of Whey Under Different Conditions," *Food Hydrocolloids* *11*(1):41-48, 1997 (BIOSIS Abstract No. 1997:408589).

Huang, M.-T., et al., "Inhibitory Effects of Curcumin on Tumorigenesis in Mice," *Journal of Cellular Biochemistry Supplement 27*:26-34, 1997 (ACS Abstract No. 129:62545).

Shankland, S.J., et al., "Mesangial Cell Proliferation Mediated by PDGF and bFGF Is Determined by Levels of the Cyclin Kinase Inhibition p27(Kip1)," *Kidney Int.* *51*(4):1088-1099, 1997 (EMBASE Abstract No. 97130705), (abstract only).

Simson, R., et al., "Evaluating the In Vivo Elastic Properties of Different Strands of Dictyostelium Discoideum Using Small Shear Forces," Technische Universität, München, Germany Abstract (BIOSIS Abstract No. 1997:441346).

* cited by examiner

METHOD FOR THE TREATMENT OF DISEASES OR DISORDERS OF THE INNER EAR

This application is a national stage filing of PCT/EP99/01153 filed Feb. 23, 1999, and claims benefit of German application 198 07 426.3, filed Feb. 23, 1998.

The invention firstly relates to a process for the treatment of diseases or disorders of the inner ear, which are linked with damage or destruction of the sensory cells of the inner ear.

The inner ear of humans and other mammals can either be irreversibly damaged from the outset by a genetic defect or subsequently by external influences. These external influences can e.g. be acoustic trauma or toxic or hypoxic influences. Such damage can lead to functional disturbances or losses of the senses located in the inner ear, particularly hearing. In the case of these functional disturbances particular reference must be made to a reduction or disappearance of the power of hearing. It is estimated that in Germany approximately 12 million people suffer from a so-called perceptive deafness, which can be attributed to the aforementioned pathogenetic mechanisms. Apart from the degeneration of sensory neurons and damage to the so-called stria vascularis of the inner ear, a cause of partial or complete loss of the power of hearing can in particular be damage or destruction of the sensory cells of the inner ear and consequently the hearing organ.

In a process for the treatment of diseases or disorders of the inner ear linked with damage or destruction of the sensory cells, it must be borne in mind that it is no longer possible to regenerate irreversibly damaged and therefore lost cells in the highly differentiated sensory epithelia in the inner ear of humans and other mammals. Thus, a partial or complete hearing loss due to damage or destruction of the sensory cells of the inner ear is generally irreversible. In this respect the sensory epithelia of the inner ear fundamentally differ from other tissues, where necrotic cells can be rapidly replaced by the division of substitute cells and their subsequent maturation.

It is of interest that in other vertebrate classes, such as e.g. birds, necrotic sensory cells in the inner ear can be regenerated, unlike the situation with humans. In birds sensory cells which have died after damage are replaced by so-called supporting cells located in the epithelium below the sensory cells. This takes place by division of the supporting cells and subsequent maturation, a new supporting cell and a sensory cell resulting from a supporting cell.

The discovery of the regeneration of sensory cells in the cochlea of the bird has over the past few years led to an attempt being made to transfer research results made on the bird to mammals and therefore ultimately humans. This inter alia promised success, because the cochlea of the bird and the cochlea of mammals have cell-biological points in common. Both the sensory epithelium of bird cochlea and the sensor epithelium of mammal cochlea are postmitotic, i.e. sensory cells present in the sensory epithelia are formed only during a specific time period of embryonic development, after which normally no further cell divisions occur. However, this fundamental point in common makes it difficult to understand the phenomenon that in the vestibular sensory epithelium of the bird cell divisions can be detected throughout its life, but not in humans.

As it was recognized in the bird that so-called growth factors can give rise to an increased proliferation rate in the bird cochlea, such growth factors were also used in the mammal cochlea. However, it was not possible to prove a reproducible action. This makes it obvious to draw the conclusion that despite fundamental cell-biological points in common, there must be other significant differences between bird and mammal cochlea. These could be that the supporting cells of the bird cochlea, as in the mammal, are postmitotic, but have only temporarily left the cell cycle. They can then reenter the cell cycle when a corresponding signal appears. Such supporting cells can be called quiescent, i.e. they are in the waiting state. As opposed to this the supporting cells of the mammal pass through a very high and specific differentiation and consequently irreversibly leave the cell cycle. They can consequently be called terminally differentiated and are e.g. comparable with neurons. This can apply in the case of the supporting cells of the mammal, which are referred to as so-called Pillar's or Deiter's cells. Such explanation models for cell-biological differences between bird and mammal cochlea have given rise to a more detailed investigation of the regeneration of the sensory cells in the bird in order to subsequently transfer the results obtained to mammals.

However, the problem of the present invention is to find a new starting point for the treatment of disorders or diseases of the inner ear, which are linked with damage or destruction of the sensory cells of the inner ear. The aim is less to transfer to mammals and in particular humans results obtained on vertebrates other than mammals and more to make available an action mechanism and corresponding active ingredients, which act directly in the cellular processes in the mammal and ultimately lead to a regeneration of the sensory cells of the inner ear.

According to the invention, the process is characterized in that at least one so-called cell cycle inhibitor present in the inner ear has its inhibiting action partly inhibited or eliminated by at least one active ingredient, which results in a regeneration of the sensory cells of the inner ear. From the patent law sense this process also incorporates the use of an active ingredient able to inhibit or eliminate the action of a cell cycle inhibitor present in the inner ear, either directly for the treatment of diseases or disorders of the inner ear or indirectly for preparing a pharmaceutical composition or a medicament for the treatment of diseases or disorders of the inner ear, said diseases/disorders being linked with damage or destruction of the sensory cells of the inner ear.

The regeneration of the sensory cells of the inner ear resulting from the process according to the invention preferably takes place through a stimulation of the proliferation of the supporting cells of the inner ear, i.e. the supporting cells also present in the sensory epithelium and usually located between and below the sensory cells. As there are one or more cell cycle inhibitors in the supporting cells of the inner ear, by inhibiting or eliminating their inhibiting action by a suitable active ingredient it is possible to initiate the cell division of the supporting cells, thereby creating a fundamental prerequisite for creating replacement or substitute cells for the necrotic or dead sensory cells. The cells resulting from the division of the supporting cells can then at least partly mature to functional sensory cells.

With regards to the sensory cells of the inner ear referred to up to now, these are preferably so-called hair sensory cells or short hair cells, which have at their upper end hair-like extensions, so-called stereocilia or small sensory hairs. These hair cells are located on the basilar membrane in the so-called corti-organ and form as so-called outer and inner hair cells the actual receptor cells for acoustic transduction in the inner ear. Both the inner and the outer hair cells are of interest for regeneration, regeneration of the outer hair cells representing a particular field of use of the invention as a result of their greater sensitivity. Those supporting cells which are anatomically particularly well associated with the inner or outer hair sensory cells can in particular be used for the active ingredient employed according to the invention. Thus, apart from outer hair sensory cells as supporting cells can be used the so-called Hensen's cells and, below the outer hair sensory cells, the so-called Deiter's cells and "outer" Pillar's cells. These Hensen's, Deiter's and outer Pillar's cells are consequently particularly suitable as replacement cells for the outer hair sensory cells. Correspondingly alongside and below the inner hair sensory cells are provided the so-called inner sulcus cells as supporting cells and within the inner hair sensory cells also the inner Pillar's cells, both being usable as replacement cells for the inner hair sensory cells. Thus, optionally a regeneration of inner or outer hair cells can be selectively initiated and influenced. Reference can be made in this connection to the relevant textbooks and articles concerning the hearing process in mammals, particularly humans. The regeneration of the hair sensory cells participating in acoustic transduction in the inner ear for the treatment of perceptive deafness in the case of damage to said sensory cells represents the main field of use of the present invention.

The cell cycle inhibitors, whose inhibiting action is to be inhibited or eliminated according to the invention, can fundamentally be different physiological substances, particularly proteins, preventing the cell passing through the normal cell cycle, including cell division. They are preferably so-called cyclin-dependent kinase inhibitors (CDKIs). It is known that during the development of an organism they are expressed to a reinforced extent during the occurrence of terminally differentiated cells and in this way prevent the reentry of the cell into the cell cycle. This would also explain the loss of the dividability of such cells with reinforced expression of cyclin-dependent kinase inhibitors. Cell cycle inhibitors and in particular cyclin-dependent kinase inhibitors of the so-called CIP/KIP family can be selectively expressed in specific cell types. Preferred cyclin-dependent kinase inhibitors are in particular the proteins referred to as $p21^{Cip1}$, $p27^{Kip1}$ and $p57^{Kip2}$. According to the invention preference is given to the cyclin-dependent kinase inhibitor $p27^{Kip1}$. As a result of the selective expression of such inhibitors and the different expression patterns resulting therefrom, the invention can be used for selectively influencing the cell cycle in a specific cell type. If e.g. in a specific cell type, such as e.g. the supporting cells in the sensory epithelium of the inner ear, $p27^{Kip1}$ is expressed selectively or at least with a significant proportion, by means of an active ingredient aimed specifically at this inhibitor, it is possible to eliminate its inhibiting action and consequently initiate or stimulate the proliferation of supporting cells. By means of a maturation of at least part of the cells resulting from the division of the supporting cells, a regeneration of the sensory cells is brought about.

As is apparent from the statements up to now, according to the invention the inner ear disease or disorder involved is in particular a so-called perceptive deafness. This is linked with the already described damage or destruction of the hair sensory cells in the inner ear.

In the case of the active ingredient usable according to the invention, which inhibits or eliminates the inhibiting action of the cell cycle inhibitor, is preferably a substance, which normally acts in intracellular manner either directly or indirectly on the inhibitor, i.e. normally a peptide or protein. The active ingredient is preferably present in the form of a peptide or protein, which effects a peptide—peptide or protein—protein interaction with the inhibitor. This would then be the case of a "direct" influencing of the function of the inhibitor. If the active ingredient is constituted by a nucleic acid molecule, which codes one of the aforementioned peptides/proteins for the amino acid sequence, it is possible to refer to an "indirect" influencing, because initially the coding nucleic acid molecule is introduced into the corresponding cell and subsequently the peptide/protein molecule (serving directly as the active ingredient) is expressed. Said nucleic acid molecule can in particular be a recombined nucleic acid molecule. The nucleic acid molecule can fundamentally be a DNA molecule, a cDNA molecule or a RNA molecule.

Another active ingredient usable in preferred manner according to the invention is a nucleic acid molecule, where use is made of the so-called antisense method. In this method which is fundamentally known to the expert use is normally made of a RNA, which is complimentary to the RNA of the normal (physiological) gene. This complimentary RNA is called antisense-RNA. The antisense-RNA can prevent the synthesis of the protein product belonging to the gene. In the case of the invention this means that a nucleic acid molecule, e.g. the antisense-RNA itself or DNA, during whose transcription the antisense-RNA is formed, is introduced into the organism or cell for inhibiting or eliminating the inhibiting action of the cell cycle inhibitor. This introduction preferably takes place with the aid of lipid compounds, which also carry viral components for the better docking and penetration of the nucleic acid molecule into the cell.

As stated, the active ingredient in the case of the invention can effect a direct interaction, preferably a peptide—peptide or protein—protein interaction with the cell cycle inhibitor. However, the active ingredient can also indirectly inhibit or eliminate the inhibiting action of the cell cycle inhibitor, in that it interacts at least as well or preferably better with a physiological interaction partner of the cell cycle inhibitor than the cell cycle inhibitor itself. This prevents the cell cycle inhibitor from evolving its physiological (inhibiting) action.

Thus, e.g. in the case of the cyclin-dependent kinase inhibitor $p27^{Kip1}$, it is known that it forms a protein complex together with the cyclin-dependent kinase CDK2 and cyclin A. There are specific points at which peptide—peptide interactions occur between the $p27^{Kip1}$ and the CDX2 or cyclin A. Thus, e.g. identification has taken place of a bonding point of very high affinity between $p27^{Kip1}$ and cyclin A and several less strong bonding points between $p27^{Kip1}$ and cyclin A or $p27^{Kip1}$ and CDK2. On extracting one of the bonding points where there is no high or very high affinity bonding/interaction, an active ingredient, preferably in the form of a further peptide/protein can be selected or developed can effect a bonding/interaction of at least as high or preferably higher affinity with one of the two interaction partners at the particular bonding point. This inhibits or prevents the standard physiological interaction, because the corresponding bonding point for the physiological interaction partner is blocked.

Thus, e.g. for a bonding point between $p27^{Kip1}$ and cyclin A, but also CDK2, an optimized peptide structure or optimized amino acid sequence can be developed for the amino acid sequence of $p27^{Kip1}$ at this point, which then bonds with a better, i.e. higher affinity with the corresponding sequence of cyclin A or CDK2 at this point. Such an optimized peptide structure e.g. and preferably comprises up to 15 amino acids and can then be directly introduced into the cell or preferably expressed in intracellular manner by an artificially introduced gene. Through the high affinity of such a peptide the interaction of the physiological peptide partner is then destroyed and the formation of the peptide complex, based on the inhibiting action of the cell cycle inhibitor is prevented. Thus, the active ingredient ensures an at least partial inhibition or a complete elimination of the inhibiting action of the cell cycle inhibitor. As a result of this process starting point of the invention the concentration of the active ingredient, particularly the peptide/protein with the corresponding amino acid sequence in the cell only has to be roughly of the same level as the corresponding concentration of the cell cycle inhibitor, whose action is to be inhibited or eliminated. As such concentrations, e.g. of $p27^{Kip1}$ are approximately 10 nM/l and roughly correspond to 1,000 to 10,000 molecules per cell, even very low concentrations can suffice for the performance of the invention. It is also important that for achieving such a concentration using gene-therapeutic methods it is sufficient to introduce only a single copy of a DNA, coding for the corresponding amino acid sequence, for each cell. Compared with other methods which have to use much higher concentrations or a larger number of DNA copies, this represents a decisive advantage.

According to a further development the process according to the invention can be performed in such a way that the active ingredient is in the form of a so-called vector or vehicle, said vector or vehicle carrying at least one of the above-described nucleic acid molecules. Preferably it is a nucleic acid molecule, which codes for the amino acid sequence of a peptide or protein serving as the active ingredient. Said vectors can be conventional viral and non-viral vectors, as are known to the expert. When using viral vectors use can be made of retroviruses, adenoviruses or adeno-associated viruses. In the case of non-viral vectors it is known that no viral DNA participates, so that here fundamentally a "bare" DNA can be introduced into a cell. However, preferably such nucleic acid molecules are packed in so-called liposomes or lipoplexes and are introduced in this form into the organism and cell. The use of non-viral vectors or lipoplexes is fundamentally preferred, because viral vectors have certain disadvantages known to the expert. As a result of the above-described use possibilities of the invention, it is here frequently possible to operate without using viral vectors, because the effectiveness of the active ingredients used is very high and it is correspondingly possible to operate with low concentrations.

In the invention the active ingredient used is preferably employed in a therapeutically active quantity. In the conventional manner this can be matched to the subject undergoing treatment and inter alia use can be made of known pharmaceutical additives. According to a further development the active ingredient used and correspondingly also the process according to the invention can be provided for local application. This makes it possible to avoid possible disadvantages of a systemic application. The target location of the process according to the invention, namely the inner ear, is particularly suitable for local application. Thus, in the present case the active ingredient can be introduced into the so-called perilymphatic space of the inner ear of the mammal, particularly human. This is a small liquid space with a very slow exchange rate, which is accessible to therapeutic intervention from the middle ear, e.g. via the membrane of the circular window. This perilymphatic space has a volume of only approximately 20 microliters and is also in direct contact with the cells of the corti-organ. This ensures a direct action of the active ingredient on the sensory epithelium with its hair cells and supporting cells.

The invention also relates to the actual active ingredient, whose use is described in detail in the above-described process. This active ingredient is intended for the regeneration of the sensory cells of the inner ear, particularly the hair sensory cells of the inner ear and is able to at least partly inhibit or eliminate the inhibiting action of a so-called cell cycle inhibitor present in the inner ear. The cell cycle inhibitor is preferably a cyclin-dependent kinase inhibitor, particularly the cyclin-dependent kinase inhibitor $p27^{Kip1}$. Reference is made to the statements hereinbefore concerning the specific, preferred characteristics of the active ingredient. As stated, it can be at least one peptide/protein or at least one nucleic acid molecule, the latter preferably being an antisense-DNA or antisense-RNA or preferably codes for a corresponding peptide/protein usable as the active ingredient. The nucleic acid molecule can be a DNA molecule, a cDNA molecule or a RNA molecule. In particular, the nucleic acid molecule is introduced with the aid of a suitable vector or vehicle into the organism or cell and these can be the described viral or non-viral vectors or nucleic acid molecules packed in liposomes/lipoplexes.

The invention finally relates to a pharmaceutical composition or medicament, which contains at least one active ingredient able to inhibit or eliminate the action of a cell cycle inhibitor present in the inner ear, in an active quantity, as well as conventionally a pharmaceutically acceptable carrier or support.

The described and further features of the invention can be gathered from the following description of a preferred embodiment in conjunction with the subclaims, the example and the drawing. The individual features can be implemented-individually or in the form of subcombinations.

FIG. 1 is an electron micrograph of a cell in nuclear division in the sensory epithelium of the corti-organ of a so-called $p27^{Kip1}$ knockout mouse.

EXAMPLE

For the test use was made of a so-called $p27^{Kip1}$ knockout mouse (p27-/-), a mouse lacking the gene for expressing the protein $p27^{Kip1}$. Thus, in such a mouse $p27^{Kip1}$ cannot evolve per se its cell cycle-inhibiting action.

The corti-organ is removed from such a $p27^{Kip1}$ knockout mouse on the seventh day after birth (postnatal day 7) and is prepared in the usual way for electron microscopic examination making it possible to see the sensory epithelium of the corti-organ.

The result of the electron microscopic examination is shown in FIG. 1. This electronic micrograph shows that a cell in nuclear division (mitosis), i.e. a mitotic cell is located between two left-hand, upper or right-hand, lower, inner hair cells, whereof the black bordered nuclei are at the left-hand top (complete) and right-hand bottom (partial). Mitosis is clearly visible on the condensed chromatin, the dissolved nuclear membrane and the basal body. the inner hair cell top left and the basal body are given English-language captions in the drawing to facilitate understanding.

FIG. 1 clearly shows that the lack of the cell cycle inhibitor $p27^{Kip1}$ leads to the possibility of a cell division of supporting cells located there in the sensory epithelium of the corti-organ of the mouse. Mention is also made of the fact that in the case of the cell division shown in FIG. 1 it is not a single phenomenon within the sensory epithelium of the corti-organ, but instead a large number of the cells there undergo a cell division and therefore pass through the cell cycle. The phenomenon shown in FIG. 1 enables the conclusion to be drawn that not only a cell division, but also following a cell division, which represents the decisive step in the hair cell regeneration process, there is also a differentiation or maturation to hair sensory cells and finally a functional recovery of the auditory function of the sensory organ. Thus, a regeneration of the sensory cells is possible. This conclusion is supported by the fact that in the case of the knockout mouse there is not a single mitosis, but instead such knockout mice have more hair cells than normal mice, in which the protein $p27^{Kip1}$ is expressed. Thus, the mitosis of the supporting cells also results in matured sensory cells. The correctness of this conclusion is confirmed by the following results. In the case of heterozygous knockout mice the regeneration of hair cells was proved in that in the second week of living of the animals when they evolve the auditory function, the hair cells were destroyed by the systemic administration of amikacin. After a further two weeks without any injection the animals were killed and their cochlea examined. This revealed regenerated hair cells in the cochlea, which are marked or labelled by a proliferation marker or label (bromodesoxyuridine—BrdU) e.g. administered with the amikacin.

Thus, not only in knockout mice where the gene for $p27^{Kip1}$ was missing from the outset, but also by inhibiting or eliminating the $p27^{Kip1}$ expressed in the normal organism, e.g. with the aid of a peptide interacting with $p27^{Kip1}$ or one of its physiological partners, with the aid of the nucleic acid sequence coding for this peptide or with the aid of an antisense-DNA/antisense-RNA it is possible to bring about a regeneration of the sensory cells. This can also take place by an only partial elimination of the function of $p27^{Kip1}$, because in the case of heterozygous mice a gene dose-dependent effect is observed.

What is claimed is:

1. A process for the treatment of hearing loss caused by damaged inner ear sensory hair cells, the process comprising the step of at least partly inhibiting or eliminating the action of $p27^{Kip1}$ present in the inner ear by local administration of antisense molecules to mammalian $p27^{Kip1}$ to the inner ear, thereby promoting regeneration of the sensory hair cells of the inner ear.

2. The process according to claim 1, characterized in that the regeneration of the sensory-hair cells of the inner ear takes place by stimulating proliferation of the supporting cells of the inner ear.

3. A process for promoting regeneration and growth of sensory hair cells in the inner ear of a mammalian subject in need thereof, the process comprising the step of locally administering antisense molecules to mammalian $p27^{Kip1}$ to the inner ear in an amount sufficient to promote regeneration and growth of sensory hair cells in the inner ear.

* * * * *

UNITED STATES PATENT AND TRADEMARK OFFICE
CERTIFICATE OF CORRECTION

PATENT NO. : 7,087,581 B1 Page 1 of 1
APPLICATION NO. : 09/622719
DATED : August 8, 2006
INVENTOR(S) : H. Loewenheim It is certified that error appears in the above-identified patent and that said Letters Patent is hereby corrected as shown below:

| COLUMN | LINE | ERROR |
|---|---|---|
| (30) Pg. 1, col. 2 | Foreign Application Priority Data | "198 07 426" should read --198 07 426.3-- |
| 8 (Claim 2, | 15 line 2) | "sensory-hair" should read --sensory hair-- |

Signed and Sealed this

Fourteenth Day of November, 2006

JON W. DUDAS
*Director of the United States Patent and Trademark Office*